(12) United States Patent
Mustafa

(10) Patent No.: US 8,523,796 B2
(45) Date of Patent: Sep. 3, 2013

(54) INFLATABLE SPLINT

(76) Inventor: Ibtesam M. Y. Mustafa, Kuwait (KW)

( * ) Notice: Subject to any disclaimer, the term of this patent is extended or adjusted under 35 U.S.C. 154(b) by 0 days.

(21) Appl. No.: 13/586,258

(22) Filed: Aug. 15, 2012

(65) Prior Publication Data

US 2013/0053740 A1 Feb. 28, 2013

Related U.S. Application Data

(63) Continuation of application No. 13/219,583, filed on Aug. 26, 2011.

(51) Int. Cl.
*A61F 5/00* (2006.01)
*A61F 13/00* (2006.01)

(52) U.S. Cl.
USPC ........... 602/13; 602/5; 602/6; 602/60; 602/61

(58) Field of Classification Search
USPC .. 602/13, 14, 19, 23, 27, 5–10; 601/148–152
See application file for complete search history.

(56) References Cited

U.S. PATENT DOCUMENTS

| | | | | |
|---|---|---|---|---|
| 891,181 | A * | 6/1908 | Mitchell | 602/13 |
| 3,901,225 | A * | 8/1975 | Sconce | 602/13 |
| 4,157,713 | A * | 6/1979 | Clarey | 602/13 |
| 4,442,834 | A * | 4/1984 | Tucker et al. | 602/13 |
| 5,288,286 | A * | 2/1994 | Davis | 602/6 |
| 2005/0203451 | A1 * | 9/2005 | Reis et al. | 602/13 |
| 2006/0189907 | A1 * | 8/2006 | Pick et al. | 602/13 |
| 2007/0197943 | A1 * | 8/2007 | Hakonson et al. | 602/13 |
| 2008/0004555 | A1 * | 1/2008 | Reis et al. | 602/13 |
| 2009/0024062 | A1 * | 1/2009 | Einarsson | 600/595 |
| 2009/0177132 | A1 * | 7/2009 | Reis et al. | 602/13 |
| 2010/0160843 | A1 * | 6/2010 | Neely | 602/13 |

FOREIGN PATENT DOCUMENTS

WO          WO 0045754 A1 *   8/2000

OTHER PUBLICATIONS

Prior art cited in parent U.S. Appl. No. 13/219,583, filed Aug. 26, 2011, the priority of which is claimed herein.

* cited by examiner

*Primary Examiner* — Kim M Lewis
(74) *Attorney, Agent, or Firm* — Richard C. Litman

(57) ABSTRACT

The inflatable splint is formed of an inner shell of thin, semi-rigid material and at least one pneumatically inflated ply surrounding the inner shell. A second pneumatically inflated ply may be placed around the first pneumatically inflated layer. The inner shell may be lined with a soft fabric material, or a soft fabric sock or sleeve may be applied over the injured limb for comfort. The innermost semi-rigid ply of the splint may be formed in two halves that attach removably to one another to allow the assembly to be removed from the wearer from time to time for hygiene, therapy, and/or other reasons as required. The pneumatically inflatable outer plies are each formed as a single wrap. An inflation device may be provided with the assembly, for the convenience of the wearer to adjust the inflation pressure of the outer pneumatic ply or plies.

20 Claims, 4 Drawing Sheets

INFLATABLE SPLINT

CROSS-REFERENCE TO RELATED APPLICATIONS

This is a continuation of my prior application Ser. No. 13/219,583, filed Aug. 26, 2011 now pending.

BACKGROUND OF THE INVENTION

1. Field of the Invention

The present invention relates to the medical field, and particularly to an inflatable splint having a semi-rigid inner ply and at least one outer ply removably attached to the inner ply, the outer ply(s) being inflatable to add rigidity and protection.

2. Description of the Related Art

The necessity of immobilizing a broken or badly sprained limb or torn ligament to provide for proper healing has been known for centuries. This has been conventionally accomplished by laying up a rigid plaster cast over and around the injured limb, with the plaster cast remaining in place for perhaps several weeks or perhaps a couple of months or more. Plaster casts are relatively heavy, and an extensive plaster cast covering the greater majority of the leg greatly reduces the mobility of the wearer of the cast due to the inability of the wearer to flex the leg and also due to the relatively high weight of the cast. While the rigidity of the injured limb is a requirement for proper healing, the high weight of a plaster cast is a major detriment to the mobility of the wearer of the cast.

As a result, the medical profession has developed lighter weight casts of fiberglass and other composite materials. Even more recently, pneumatically inflatable casts and splints of even lighter weight have been developed. While such lightweight casts are considerably more comfortable for the wearer due to the greater ease of movement provided, they are generally still permanently installed on the limb for the duration of the healing process, and they cannot be adjusted or removed. Anyone who has worn a cast for any period of time recognizes the great inconvenience caused by such a cast, regardless of its weight and construction. Bathing and other hygiene can be difficult to nearly impossible with some casts, depending upon their materials, their location on the body, and the extent of the cast. Plaster casts must be protected from water, so the wearer cannot bathe more thoroughly than by means of a "sponge bath" on areas of the body not encased by the cast, while wearing such a cast. While more modern materials may be wetted without harm, they still must remain in place and water that becomes entrapped between the cast and the surface of the skin can lead to additional problems for the wearer.

Thus, an inflatable splint solving the aforementioned problems is desired.

SUMMARY OF THE INVENTION

The inflatable splint has several forms intended for application to different parts of the body. Each embodiment of the inflatable splint includes an inner layer or ply formed of a semi-rigid, thin inner shell and at least one additional pneumatically inflatable layer or ply that is secured about the semi-rigid, thin inner shell. A second pneumatically inflatable layer or ply may be placed about the first pneumatically inflatable layer or ply, to form three layers or plies for the cast or splint assembly. The inner shell may be lined with a soft fabric liner, or alternatively a soft fabric sock or sleeve may be applied to the injured limb or other area of the body prior to installing the shell and pneumatically inflated components.

The innermost semi-rigid layer or ply comprises a pair of mutually opposed, mating portions that secure to one another about the injured limb or other body part of the wearer. The two portions may be detached from one another as desired, to access the injured limb for therapy, cleaning, and/or other purposes as required. The inner ply, although made of molded plastic or fiberglass, has sufficient flexibility to allow the ply to curve around a fractured arm or limb, but sufficient rigidity to at least partially immobilize the limb; hence, the term semi-rigid. Alternatively, the semi-rigid inner ply may be formed as a single, unitary component in some instances, depending upon the area of the body to which the device is to be applied. The outer, pneumatically inflatable layers or plies may each be formed as a single wrap or cuff, somewhat in the manner of a blood pressure test cuff.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The inflatable splint comprises several embodiments of a splint for application to various parts of the body. Each of the embodiments includes a thin, semi-rigid inner shell, preferably formed in two halves or portions that secure around the injured limb or other portion of the body immediately adjacent to the skin. The inner shell has sufficient flexibility to conform to the injured or fractured limb, but sufficient rigidity to at least partially immobilize the limb; hence, the term semi-rigid. At least one flexible, resilient, pneumatically inflatable overlay is wrapped around and over the shell assembly and secured thereover. The overlay may then be inflated to add further rigidity to the assembly and to provide further protection for the injury.

Figure 1:
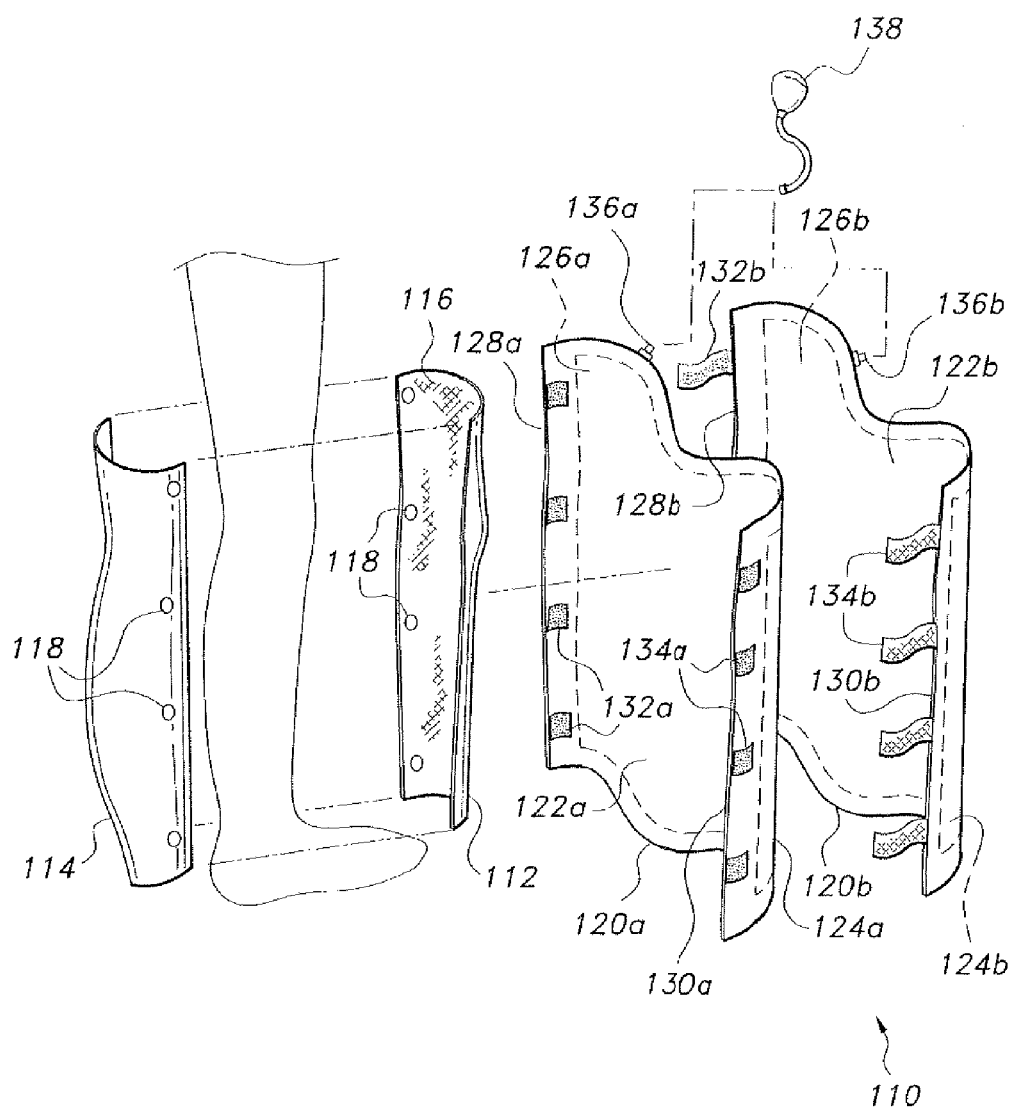
FIG. 1 is an exploded perspective view of a first embodiment of an inflatable splint according to the present invention, illustrating its general configuration.

FIG. 1 of the drawings illustrates a first embodiment of the inflatable splint. The inflatable splint 110 of FIG. 1 is configured for placement over an injured leg. The inflatable splint 110 includes a thin, semi-rigid, anatomically conforming inner shell formed of plastic, glass fiber composite, carbon fiber composite, or other suitably lightweight thin material. The shell is formed as a forward half or portion 112 and an opposite rearward half or portion 114 in the exemplary embodiment of FIG. 1. It will be seen that the shell components 112 and 114 may be formed as two lateral portions, or otherwise portioned, as desired. The shell components 112 and 114 may be configured in several sizes to fit various sizes of individuals, from smaller children to larger adults. The shell components 112 and 114 are preferably lined or covered with a soft knit or woven fabric material 116, for the comfort of the wearer. Alternatively, a conventional sock or sleeve extending the length of the shell components 112 and 114 may be applied to the body before the shell components 112 and 114 are installed. The two components 112 and 114 are secured to one another by means of cooperating snap fasteners 118 or other releasable fasteners, e.g., mating hook and loop fabric material, as used with other components of the splint. The fasteners 118 (or other attachments) allow the shell components 112 and 114 to be removed from time to time, as may be required for hygiene, treatment of surface wounds, physical therapy, etc.

First and second pneumatically inflated overlays, respectively 120a and 120b, are configured to wrap around the two shell portions 112 and 114 after they have been placed upon the patient. In some applications it may be sufficient to place only a single inflatable overlay about the underlying semi-rigid shell components, but two such overlays are illustrated in the exemplary embodiment of FIG. 1. The overlays 120a and 120b each comprise an inner sheet, respectively 122a and 122b, and an outer sheet, respectively 124a and 124b. The respective inner and outer sheets, i.e., 122a, 124a for the first overlay 120a and 122b, 124b for the second overlay 120b, are sealed to one another along their respective contiguous peripheries. The sealed peripheries define an air bladder within each overlay, designated air bladder 126a for the first overlay 120a and air bladder 126b for the second overlay 120b. The extents of the air bladders 126a, 126b are indicated in broken lines within their respective pneumatically inflated overlays 120a and 120b in FIG. 1. The various inner and outer sheets 122a, 122b and 124a, 124b are formed of a resilient, substantially leakproof material, such as a natural or synthetic elastomer (rubber, neoprene, etc.).

The laterally opposed edges 128a and 130a of the overlay 120a include mating hook and loop fabric fasteners disposed thereon for adjustably securing the two edges 128a, 130a to one another after wrapping the overlay 120a about the semi-rigid shell portions 112 and 114. The first overlay 120a includes mating first and second hook and loop fabric attachments 132a and 134a disposed along the respective first and second lateral edges 128a and 130a of the overlay. Similar fasteners comprising mating first and second hook and loop fabric straps 132b and 134b extend from the opposite edges 128b and 130b of the second or outermost overlay 120b. It will be seen that the hook and loop fabric tabs or patches 132a, 134a of the first overlay 120a and the hook and loop fabric straps 132b, 134b of the second overlay 120b may be interchanged, if desired, and/or other suitable securing means (e.g., snaps, ties, etc.) may be provided. Inflation valves, respectively 136a and 136b, are provided at some points on each of the overlays 120a and 120b, permitting the overlays to be inflated to the desired pressure and firmness. An inflation device 138, e.g., a manually actuated squeeze bulb similar to the inflation devices provided with blood pressure testing cuffs, or an air pump, may be provided to inflate the two overlays 120a and 120b. Other types of powered or manually operated inflation devices may be used in lieu of the device 138, as desired.

Figure 2:
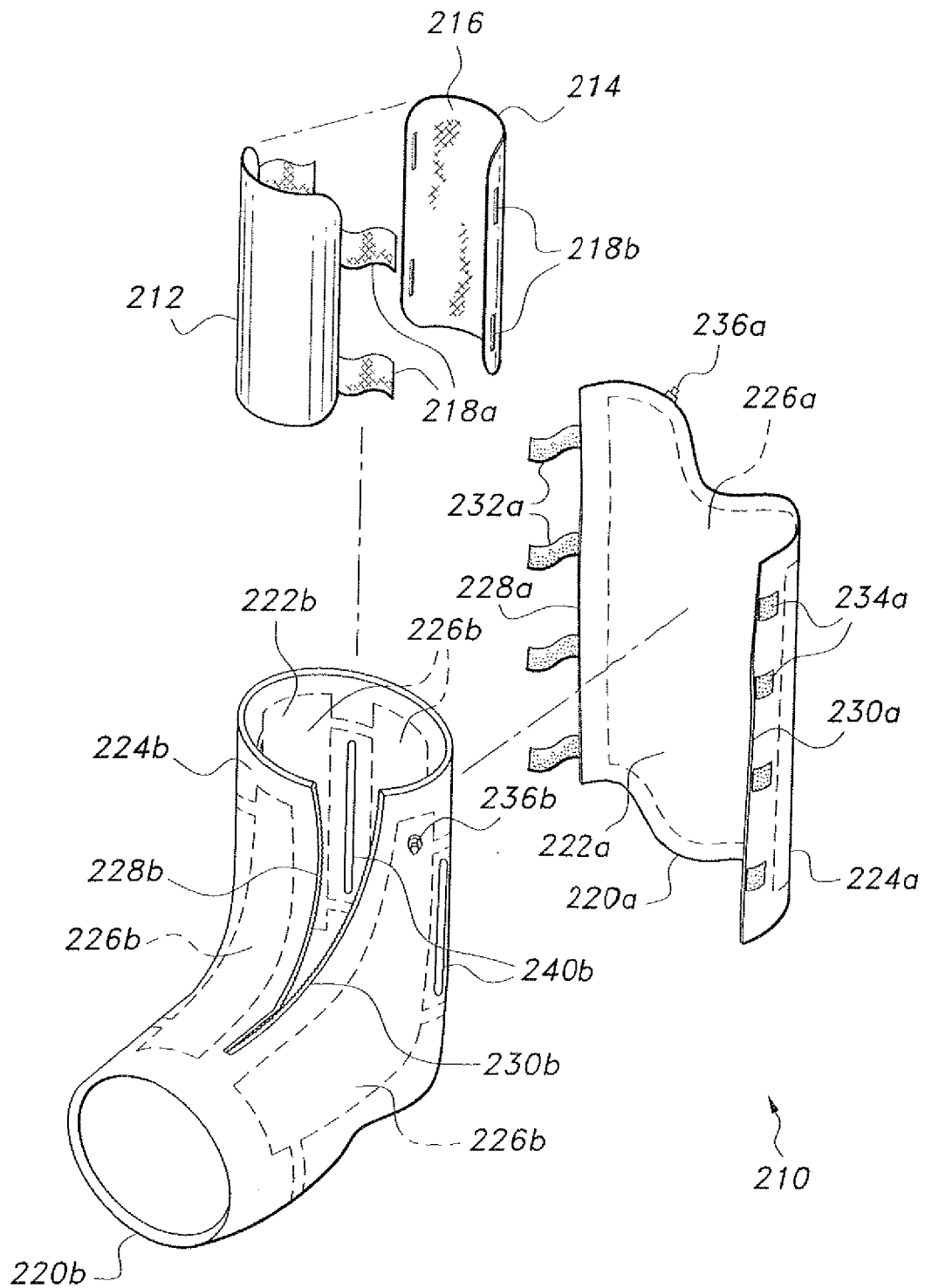
FIG. 2 is an exploded perspective view of a second embodiment of an inflatable splint according to the present invention, illustrating various features thereof.

FIG. 2 of the drawings illustrates a second embodiment of an inflatable splint comprising an inflatable splint 210 for the ankle, foot, and/or lower leg. The inflatable splint 210 of FIG. 2 is configured similar to the inflatable splint 110 of FIG. 1, having first and second semi-rigid shell portions 212 and 214 that secure about the lower leg or ankle immediately adjacent the skin. The two shell portions 212 and 214 may be formed the same materials as used for the shell portions 112 and 114 of FIG. 1, and may be formed as forward and rearward halves, lateral halves, or other portions, as desired. The shell components 212 and 214 are configured in several sizes to fit various sizes of individuals, and are preferably lined or covered with a soft knit or woven fabric material 216 for the comfort of the wearer. A sock or sleeve may be applied to the body before the shell components 212 and 214 are installed, if desired, as in the case of the inflatable splint assembly 110 of FIG. 1. The two components 212 and 214 secure to one another by means of straps 218a extending from the first shell portion 212, the straps 218a engaging cooperating slots 218b along the edges of the second shell portion 214. The straps 218a preferably include mating hook and loop fabric portions that fold back to fasten to themselves when doubled back through the slots 218b. In this manner, the straps 218a, 218b (or other attachments) allow the shell components 212 and 214 to be removed from time to time, as may be required.

A first pneumatically inflated overlay 220a is configured to wrap around the two shell portions 212 and 214 after they have been placed upon the patient. The overlay 220a comprises an inner sheet 222a and an outer sheet 224a, sealed to one another along their respective contiguous peripheries. The sealed peripheries define an air bladder 226a within the overlay, the extent of the air bladder 226a being indicated in broken lines. The inner and outer sheets 222a and 224a are formed of a resilient, substantially leakproof material, such as a natural or synthetic elastomer (rubber, neoprene, etc.).

The first edge 228a of the overlay 220a includes hook and loop fabric straps 232a extending therefrom, and the opposite second edge 230a has corresponding mating hook and loop fabric tabs or patches 234a disposed therealong. The straps 232a secure to the cooperating tabs 234a to secure the inflatable overlay 220a about the two shell components 212 and 214. Other fasteners may be provided, if desired, as noted in the detailed description of the two inflatable overlays 120a and 120b illustrated in FIG. 1 of the drawings. An inflation valve 236a is provided at some point on the overlay 220a, permitting the overlay to be inflated to the desired pressure or firmness. An inflation device 138, e.g., a manually actuated squeeze bulb, as illustrated in FIG. 1, may be provided to inflate the overlay 220a, or an air pump of other inflation device may be used in lieu thereof.

The second or outermost inflatable overlay 220b is configured to conform generally to the shape of the anatomy to which it is to be secured, e.g., the ankle, generally as shown in FIG. 2. The second, outermost inflatable overlay 220b is preferably formed as a unitary component, and is secured over the first inflatable overlay 220a after it has been placed over the two shell components 212 and 214. The second overlay 220b also comprises an inner sheet 222b and an outer sheet 224b, which are formed of a resilient, substantially leakproof material, such as a natural or synthetic elastomer (rubber, neoprene, etc.). The two sheets 222b, 224b are sealed to one another along their respective contiguous peripheries and at various points therebetween. The sealed peripheries and intermediate points define a plurality of interconnected air bladders or chambers 226b within the overlay, the extent of the air bladders 226b being indicated in broken lines. The areas between adjacent air bladders or chambers 226b may include ventilation passages 240b therethrough, if desired. The ventilation passages 240b may be in the form of elongate slots, as shown, or some other configuration, e.g., smaller circular passages or other shape(s), depending upon the shapes and configurations of the interconnected air bladders or chambers 226b. It will be seen that the air bladder 226a of the first pneumatically inflatable overlay 220a may comprise a series of interconnected chambers with ventilation passages disposed therebetween, if desired, similar to the configuration of the second or outer overlay 220b. For that matter, the first and/or second pneumatically inflatable overlays 120a and 120b of FIG. 1 may have similarly configured inflatable bladders or chambers and ventilation passages, if desired.

The second or outer overlay 220b further includes laterally opposed first and second edges 228b and 230b extending from one end of the overlay partially toward the opposite distal end. The distal end forms a circumferentially closed sleeve having an open end for toe clearance. Alternatively, the distal end may be completely closed. The two edges 228b, 230b may comprise mating rows of zipper teeth selectively closed by a conventional zipper slider, or other mating means of joining the two edges. An inflation valve 236b is provided at some point on the outer or second overlay 220b, permitting the overlay to be inflated. An inflation device 138, e.g., a manually actuated squeeze bulb, as illustrated in FIG. 1, may be provided to inflate the overlay 220b as desired. Other types of powered or manually operated inflation devices may be used in lieu of the device 138.

Figure 3:
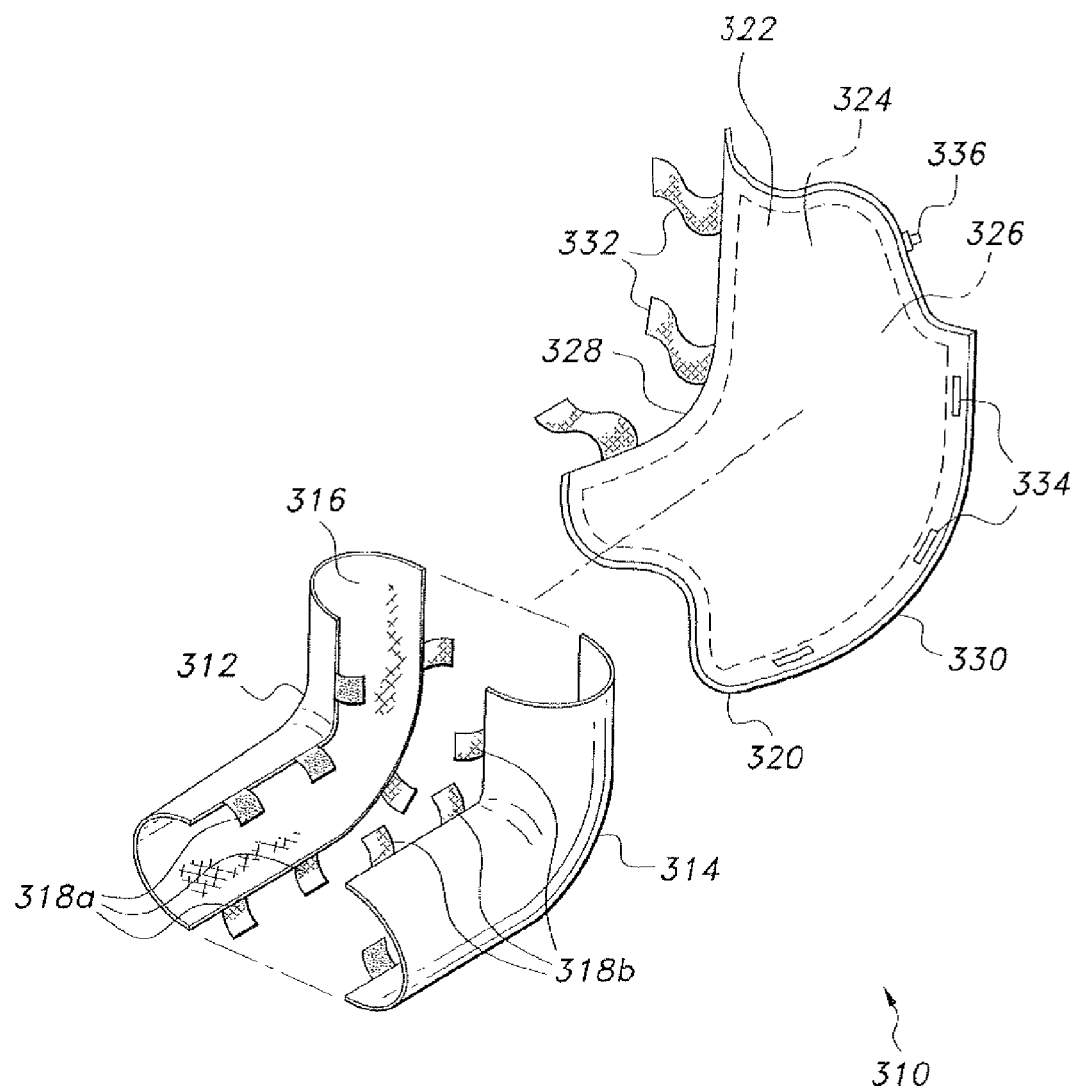
FIG. 3 is an exploded perspective view of a third embodiment of an inflatable splint according to the present invention, illustrating various features thereof.

FIG. 3 of the drawings illustrates a third embodiment of the inflatable splint, designated as inflatable splint 310. The inflatable splint 310 is configured to fit about the elbow of the wearer or patient, the device extending at least partially upward along the upper arm toward the shoulder and at least partially downward along the lower arm toward the wrist. As in the case of the other embodiments of the inflatable splint, the splint 310 includes a two-part inner shell formed of thin sheets of semi-rigid material. The two shell components 312 and 314 are preferably lined with a soft fabric liner 316, as in the case of other embodiments. The two components or portions 312 and 314 have cooperating fasteners 318a and 318b, e.g., mating hook and loop fabric material, extending from their mating peripheries. Alternative fasteners, e.g., tabs, snaps, ties, etc. may be provided.

The inflatable splint 310 of FIG. 3 includes only a single pneumatically inflated overlay 320, rather than having two such overlays, as in the embodiments of FIGS. 1 and 2. However, it will be seen that another outer overlay (not shown in FIG. 3) may be provided for the splint 310 of FIG. 3, if desired. The pneumatically inflated overlay 320 is configured to wrap around the two shell portions 312 and 314 after they have been placed upon the patient. The overlay 320 comprises an inner sheet 322 and an outer sheet 324, sealed to one another along their respective contiguous peripheries. The sealed peripheries define an air bladder 326 within the overlay, the extent of the air bladder 326 being indicated in broken lines. The inner and outer sheets 322 and 324 are formed of a resilient, substantially leakproof material, such as a natural or synthetic elastomer (rubber, neoprene, etc.).

The two opposite edges 328 and 330 of the overlay 320 are secured to one another by means of straps 332 extending from the first edge 328, the straps 332 engaging cooperating slots 334 along the opposite edge 330, in the manner of the strap and slot arrangement of the two shell portions 212 and 214 of the second embodiment of the inflatable splint, illustrated in FIG. 2. The straps 332 preferably include mating hook and loop fabric portions that fold back to fasten to themselves when doubled back through the slots 334. The strap and slot attachment means illustrated in FIG. 3 is exemplary, and other releasable fasteners may be provided, as noted in the detailed description of the two inflatable overlays 120a and 120b illustrated in FIG. 1 of the drawings. An inflation valve 336 is provided at some point on the overlay 320, permitting the overlay to be inflated. An inflation device 138, e.g., a manually actuated squeeze bulb as illustrated in FIG. 1, may be provided to inflate the overlay 320. Other types of powered or manually operated inflation devices may be used in lieu of the device 138, as noted further above.

Figure 4:
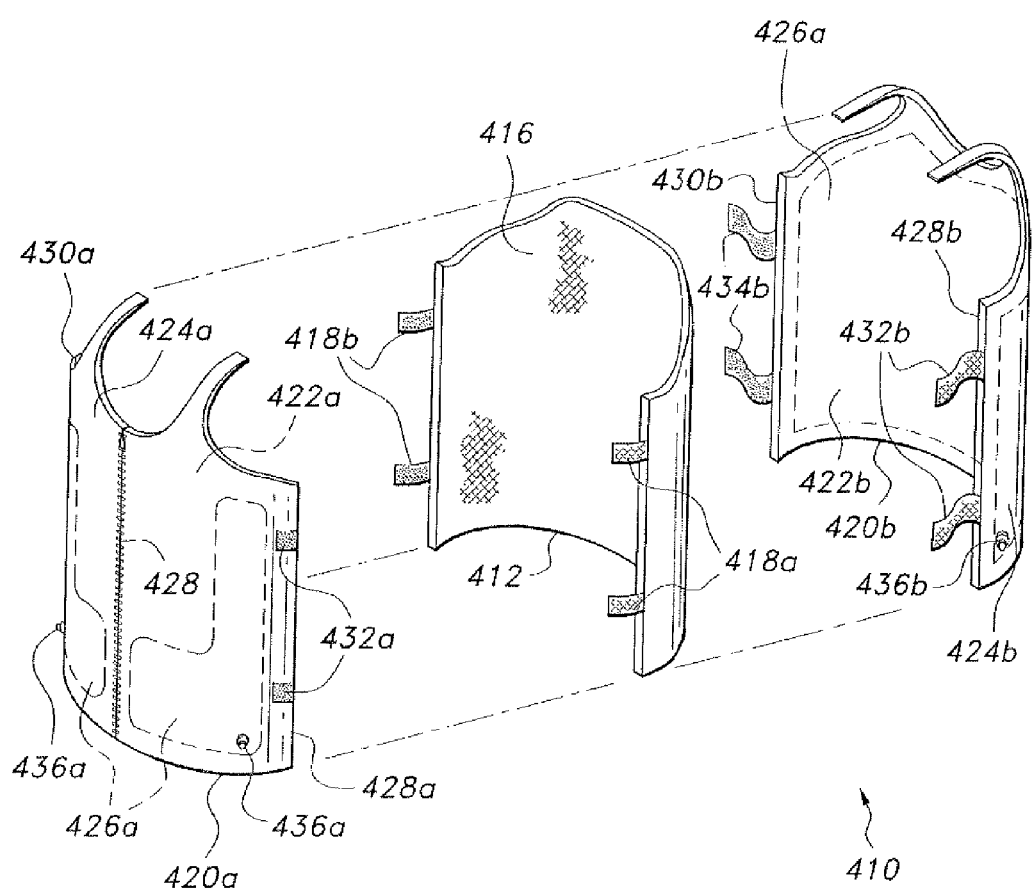
FIG. 4 is an exploded perspective view of a fourth embodiment of an inflatable splint according to the present invention, illustrating various features thereof.

FIG. 4 of the drawings illustrates a fourth embodiment of the inflatable splint, designated as inflatable splint 410. The inflatable splint 410 is configured to fit about the torso of the wearer or patient. Rather than having a two-part semi-rigid shell, as in the other embodiments, the inflatable splint 410 includes only a single, dorsal shell component 412, in order to avoid restriction of chest movement and respiratory function. The dorsal shell component 412 is preferably lined with a soft fabric liner 416, as in the case of other embodiments. Alternatively, or in addition, the wearer of the device may don a soft T-shirt or other comfortable garment before donning the dorsal shell 412. The shell 412 has cooperating fasteners 418a and 418b, e.g., mating hook and loop fabric material, extending from its opposite left and right edges. Alternative fasteners, e.g., tabs, snaps, ties, etc. may be provided, if desired. These fasteners 418a and 418b enable the two pneumatically inflated overlays 420a and 420b to be attached to the shell 412 and around the torso of the wearer, as explained further below.

First and second pneumatically inflated overlays, respectively 420a and 420b, are configured to extend across the chest and back of the patient or wearer. The overlays 420a and 420b each comprise an inner sheet, respectively 422a and 422b, and an outer sheet, respectively 424a and 424b. The respective inner and outer sheets, i.e., 422a, 424a for the first or front overlay 420a and 422b, 424b for the second overlay 420b, are sealed to one another along their respective contiguous peripheries. The sealed peripheries define at least one air bladder within each overlay, designated left and right air bladders 426a for the first overlay 420a, and a single air bladder 426b for the second overlay 420b. The extents of the air bladders 426a, 426b are indicated in broken lines within their respective pneumatically inflated overlays 420a and 420b in FIG. 4. It will be noted that the two air bladders 426a of the first or forward overlay 420a do not extend upward over the center of the chest area. This is in order to avoid restricting chest movement for respiration when the pneumatic bladders 426a are firmly and fully inflated. The various inner and outer sheets 422a, 422b and 424a, 424b are formed of a resilient, substantially leakproof material, such as a natural or synthetic elastomer (rubber, neoprene, etc.), as in the case of the other embodiments.

The front or first pneumatically inflatable overlay 420a is actually formed as a left and a right portion, the two portions being selectively joined by a zipper 428. The laterally opposed edges 428a and 430a of the first or front overlay 420a include mating hook and loop fabric fasteners disposed thereon for adjustably securing the corresponding tabs or straps 418a and 418b of the dorsal shell 412 to the front overlay. Similar mating first and second hook and loop fabric straps 432b and 434b extend from the opposite edges 428b and 430b of the second or dorsal overlay 420b. It will be seen that the hook and loop fabric tabs or patches, e.g., left side or edge tabs 432a, of the first overlay 420a and the hook and loop fabric straps 432b, 434b of the second overlay 420b, may be interchanged, and/or other suitable releasable fasteners (e.g., snaps, ties, etc.) may be provided.

Inflation valves, respectively 436a and 436b, are provided at some points on each of the overlays 420a and 420b, permitting the overlays to be inflated. An inflation device 138, e.g., a manually actuated squeeze bulb as shown in FIG. 1, may be provided to inflate the two overlays 420a and 420b. It should be noted that the provision of a zipper 428 or other means of separably joining the left and right portions of the forward or first pneumatic overlay 420a would permit the forward and rearward overlays 420a and 420b to be constructed as a unitary component, if so desired. Such a single pneumatic overlay could be donned and removed like a vest, and the shoulder straps of the forward and rearward portions may be separable to facilitate donning or removal of the device by a person with limited mobility. Such a unitary pneumatic overlay may be provided with only a single inflation valve, if all of the inflation bladders are interconnected.

It is to be understood that the present invention is not limited to the embodiments described above, but encompasses any and all embodiments within the scope of the following claims.

I claim:

1. An inflatable splint, comprising:
a thin, semi-rigid, anatomically conforming inner shell adapted for removable placement upon a portion of a human body, the inner shell having mating releasable fasteners for facilitating selective removable placement upon the portion of the human body; and
at least one pneumatically inflatable overlay, the overlay being adapted for removable placement over the inner shell, the overlay having mating releasable fasteners for facilitating selective removable placement over the inner shell, the inner shell and the overlay forming a splint immobilizing and protecting the portion of the human body during healing when the overlay is inflated.

2. The inflatable splint according to claim 1, wherein the at least one pneumatically inflatable overlay comprises a first overlay and a second overlay, the second overlay being removably disposed over the first overlay.

3. The inflatable splint according to claim 1, wherein:
the inner shell comprises a first portion and a second portion, the first and second portions being removably secured to one another; and
the at least one pneumatically inflatable comprises a single wrap having mutually opposed lateral edges, the lateral edges being removably secured to one another.

4. The inflatable splint according to claim 1, further comprising:
at least one inflation valve disposed upon the at least one pneumatically inflated overlay; and
an inflation device pneumatically cooperating with the at least one inflation valve.

5. The inflatable splint according to claim 1, further comprising a soft knit fabric liner disposed within the inner shell.

6. The inflatable splint according to claim 1, wherein the at least one pneumatically inflatable is formed of a material selected from the group consisting of natural and synthetic elastomers.

7. The inflatable splint according to claim 1, wherein the at least one pneumatically inflated overlay has at least one ventilation passage disposed therethrough.

8. An inflatable splint, comprising:
a first pneumatically inflated, anatomically conforming overlay adapted for removable placement upon a portion of a human body, the first overlay having mating releasable fasteners for facilitating selective removable placement upon the portion of the human body; and
a second pneumatically inflated, anatomically conforming overlay, the second overlay being removably disposed over the first overlay, the second overlay having mating releasable fasteners for facilitating selective removable placement over the first overlay, the first and second overlays forming a splint for immobilizing and protecting the portion of the human body when the first and second overlays are inflated.

9. The inflatable splint according to claim 8, further comprising a thin, semi-rigid, anatomically conforming inner shell adapted for removable placement upon a portion of the anatomy, the inner shell being disposed beneath the first overlay.

10. The inflatable splint according to claim 9, wherein:
the inner shell comprises a first portion and a second portion, the first and second portions being removably secured to one another; and
each of said first and second pneumatically inflated overlay comprises a single wrap having mutually opposed lateral edges, the lateral edges being removably secured to one another.

11. The inflatable splint according to claim 9, further comprising a soft knit fabric liner disposed within the inner shell.

12. The inflatable splint according to claim 8, further comprising:
an inflation valve disposed upon each of said first and second pneumatically inflated overlay; and
an inflation device pneumatically cooperating with the inflation valve.

13. The inflatable splint according to claim 8, wherein each said pneumatically inflated overlay is formed of a material selected from the group consisting of natural and synthetic elastomers.

14. The inflatable splint according to claim 8, wherein at least one of said pneumatically inflated overlay has at least one ventilation passage disposed therethrough.

15. An inflatable splint, comprising:
a thin, semi-rigid, anatomically conforming inner shell adapted for removable placement upon a portion of a human body, the inner shell having mating releasable fasteners for facilitating selective removable placement upon the portion of the human body;
a first pneumatically inflated overlay removably disposed over the inner shell, the first overlay having mating releasable fasteners for facilitating selective removable placement over the inner shell; and
a second pneumatically inflated overlay removably disposed over the first overlay, the second overlay having mating releasable fasteners for facilitating selective removable placement over the first overlay, the inner shell, the first overlay, and the second overlay forming a splint for immobilizing and protecting the portion of the human body when the first and second overlays are inflated.

16. The inflatable splint according to claim 15, wherein:
the inner shell comprises a first portion and a second portion, the first and second portions being removably secured to one another; and
each said pneumatically inflated overlay comprises a single wrap having mutually opposed lateral edges, the lateral edges being removably secured to one another.

17. The inflatable splint according to claim 15, further comprising a soft knit fabric liner disposed within the inner shell.

18. The inflatable splint according to claim 15, further comprising:
an inflation valve disposed upon each said pneumatically inflated overlay; and
an inflation device pneumatically cooperating with the inflation valve.

19. The inflatable splint according to claim 15, wherein each said pneumatically inflated overlay is formed of a material selected from the group consisting of natural and synthetic elastomers.

20. The inflatable splint according to claim 15, wherein at least one of said pneumatically inflated overlay has at least one ventilation passage disposed therethrough.

* * * * *